US009063113B2

(12) United States Patent
DiFoggio

(10) Patent No.: US 9,063,113 B2
(45) Date of Patent: Jun. 23, 2015

(54) THERMAL H2S DETECTION IN DOWNHOLE FLUIDS

(71) Applicant: Rocco DiFoggio, Houston, TX (US)

(72) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 9 days.

(21) Appl. No.: 13/752,917

(22) Filed: Jan. 29, 2013

(65) Prior Publication Data

US 2014/0212983 A1 Jul. 31, 2014

(51) Int. Cl.
*G01N 33/00* (2006.01)
*G01N 33/24* (2006.01)

(52) U.S. Cl.
CPC ............... *G01N 33/24* (2013.01); *Y10T 436/18* (2015.01)

(58) Field of Classification Search
CPC .............................. G01N 33/24; Y10T 436/18
USPC ............................................. 436/119; 422/83
See application file for complete search history.

(56) References Cited

U.S. PATENT DOCUMENTS

| 4,027,002 | A |   | 5/1977 | Powlesland et al. |
| 4,344,842 | A |   | 8/1982 | Fox |
| 5,057,291 | A | * | 10/1991 | Fisher et al. .................. 423/219 |
| 5,358,921 | A |   | 10/1994 | Kidd et al. |
| 7,520,160 | B1 |   | 4/2009 | Toribio et al. |
| 2005/0199401 | A1 | * | 9/2005 | Patel et al. ..................... 166/387 |
| 2005/0205256 | A1 |   | 9/2005 | DiFoggio |
| 2007/0185467 | A1 | * | 8/2007 | Klofta et al. .................. 604/361 |
| 2008/0066534 | A1 |   | 3/2008 | Reid et al. |
| 2008/0066536 | A1 |   | 3/2008 | Goodwin et al. |
| 2008/0066904 | A1 |   | 3/2008 | Van Hal et al. |
| 2010/0212891 | A1 | * | 8/2010 | Stewart et al. ........... 166/250.12 |
| 2012/0129267 | A1 | * | 5/2012 | Daly ............................. 436/119 |

FOREIGN PATENT DOCUMENTS

EP    1308174 A1    5/2003

OTHER PUBLICATIONS

Carnes & Klabunde "Unique Chemical Reactivities of Nanocrystalline Metal Oxides toward Hydrogen Sulfide", Chem. Mater., 2002, 14 (4), pp. 1806-1811.
Notification of Transmittal of the International Search Report and the Written Opinion of the International Searching Authority, or the Declaration; PCT/US2014/013560; Mailed May 13, 2014, 19 pages.

(Continued)

*Primary Examiner* — Rebecca M Fritchman
(74) *Attorney, Agent, or Firm* — Cantor Colburn LLP

(57) ABSTRACT

An apparatus for detecting a chemical of interest in a fluid or estimating a concentration of the chemical in the fluid includes: a carrier configured to be conveyed through a borehole penetrating an earth formation; a first temperature sensor disposed at the carrier and configured to sense a temperature of the fluid and provide a first temperature output; and a second temperature sensor disposed at the carrier and covered with an exothermic reaction material that experiences an exothermic reaction when exposed to the chemical of interest and configured to sense a temperature and provide a second temperature output. The apparatus further includes a processor coupled to the first temperature sensor and the second temperature sensor and configured to detect the chemical or estimate the concentration using the first temperature output and the second temperature output.

21 Claims, 4 Drawing Sheets

(56) References Cited

OTHER PUBLICATIONS

IP Hydrocarbon Management, "HM 40 Guidelines for the Crude Oil Washing of Ships' Tanks and the Heating of Crude Oil Being Transported by Sea". 2nd edition, Jun. 2004. 75 pages.

Sayyadnejad, Ghaffarian, Saeidi, "Removal of hydrogen sulfide by zinc oxide nanoparticles in Drilling Fluid", Int. J. Environ. Sci. Tech., 5 (4), 565-569, Autumn 2008.

Sulfur removal technology, Zinc oxide adsorbent (Zn-9201E). Engelhard. Product Infromation. www.engelhard.com. 2 pp., (2005).

* cited by examiner

THERMAL H2S DETECTION IN DOWNHOLE FLUIDS

BACKGROUND

Hydrogen sulfide is a toxic and corrosive gas. It can diffuse into drilling fluid from earth formations during the drilling of boreholes such as for oil and gas wells. Hydrogen sulfide that is present in a high enough concentration may require removal and special handling. Downhole concentrations of hydrogen sulfide can vary widely. Hence, it would be important to determine the concentration of hydrogen sulfide downhole in order to efficiently plan for well production. It would be well received in the drilling and geophysical exploration industries if a downhole sensor for detecting and measuring a concentration of hydrogen sulfide could be developed.

BRIEF SUMMARY

Disclosed is an apparatus for detecting a chemical of interest in a fluid or estimating a concentration of the chemical in the fluid, The apparatus includes a carrier configured to be conveyed through a borehole penetrating an earth formation, a first temperature sensor disposed at the carrier and configured to sense a temperature of the fluid and provide a first temperature output, and a second temperature sensor disposed at the carrier and covered with an exothermic reaction material that experiences an exothermic reaction when exposed to the chemical of interest and configured to sense a temperature and provide a second temperature output. The apparatus further includes a processor coupled to the first temperature sensor and the second temperature sensor and configured to detect the chemical or estimate the concentration using the first temperature output and the second temperature output.

Also disclosed is a method for detecting a chemical of interest in a fluid or estimating a concentration of the chemical of interest in the fluid. The method includes: conveying a carrier through a borehole penetrating an earth formation; sensing a first temperature using a first sensor disposed at the carrier and configured to be immersed in the fluid and to sense a temperature of the fluid to provide a first temperature output; sensing a second temperature using a second temperature sensor disposed at the carrier and coated with an exothermic reaction material that experiences an exothermic reaction when exposed to the chemical of interest and configured to be immersed in the fluid to provide a second temperature output; and detecting with a processor the chemical using the first temperature output and the second temperature output or estimating with the processor the concentration using the first temperature output and the second temperature output.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are apparatus and method for detecting a chemical of interest in a fluid or estimating a concentration of the chemical in the fluid downhole. It can be appreciated that determining the concentration of the chemical inherently includes detecting the presence of the chemical. At least two temperature sensors are used. One temperature sensor is coated or covered with a material that undergoes an exothermic reaction with the chemical of interest when exposed to the chemical of interest. The other temperature sensor is uncoated and provides a reference temperature measurement. When both sensors are exposed to the chemical of interest, the coated sensor will heat up due to the exothermic reaction and measure a higher temperature than the uncoated sensor. In that the rate of the exothermic reaction is dependent on the concentration of the chemical of interest in the fluid, a temperature difference between the coated and uncoated sensors will provide an estimate of the concentration of the chemical of interest in the fluid. In principle, the coating could also react endothermically with the chemical of interest, but endothermic reactions are much rarer and generally have a much smaller change in energy than do exothermic ones.

Figure 1:
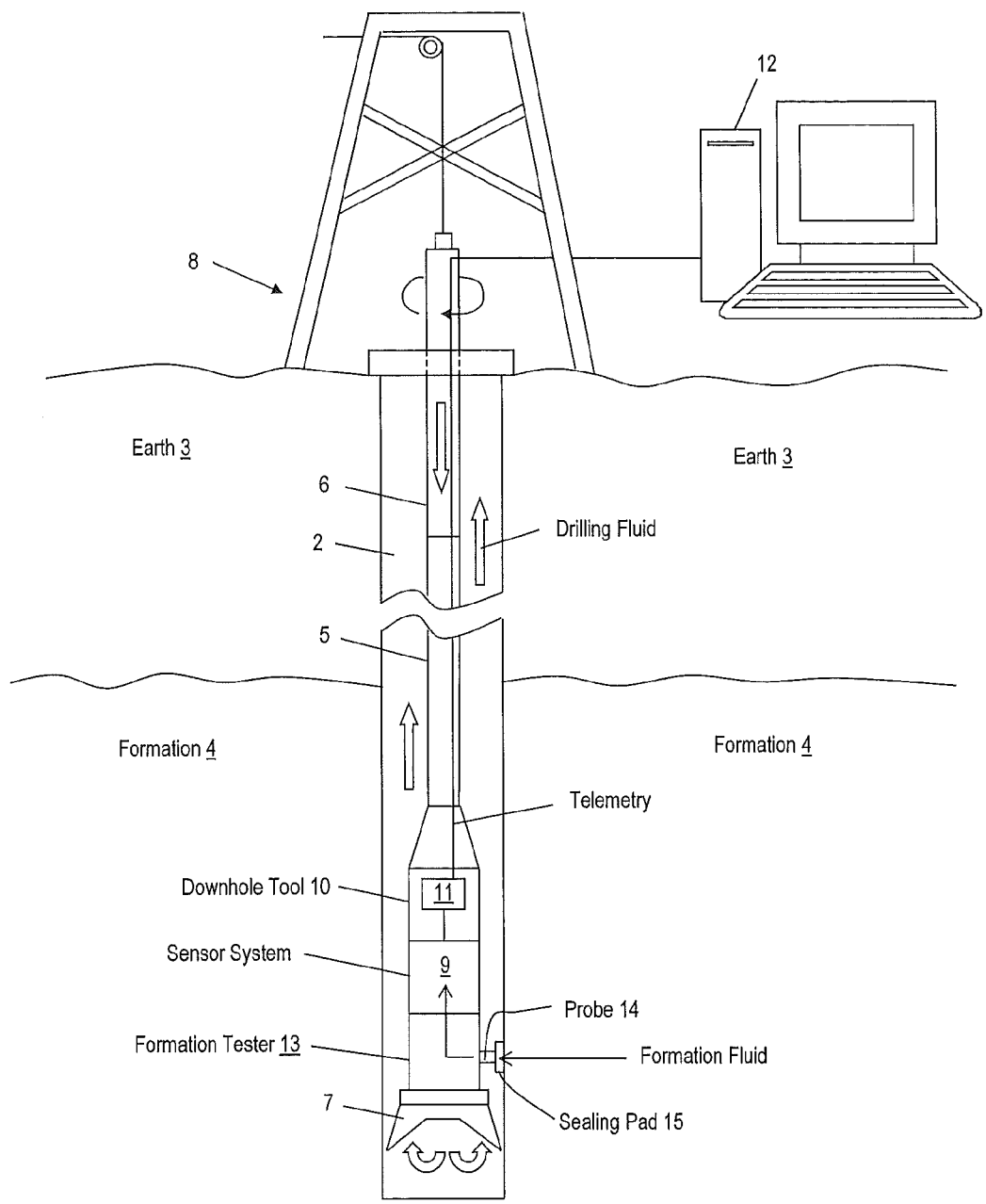
FIG. 1 illustrates a cross-sectional view of an exemplary embodiment of a downhole tool disposed in a borehole penetrating the earth.

FIG. 1 illustrates a cross-sectional view of an exemplary embodiment of a downhole tool 10 disposed in a borehole 2 penetrating the earth 3, which may include an earth formation 4. The formation 4 represents any subsurface material of interest that may be sensed by the tool 10. The downhole tool 10 includes a sensor system 9 that is configured to detect a chemical of interest in a downhole fluid or a concentration of the chemical of interest in the fluid. Non-limiting examples of the fluid include a borehole fluid such as a drilling fluid or mud or a formation fluid. The downhole tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling fluid through the drill string 6 in order to lubricate the drill bit 7 and flush cuttings from the borehole 2. Downhole electronics 11 are configured to operate the sensor system 9, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe. System operation and data processing operations may be performed by the downhole electronics 11, the computer processing system 12, or a combination thereof. The sensor system 9 may be operated continuously or at discrete selected depths in the borehole 2. In an alternative embodiment, the carrier 5 may be an armored wireline, which can also provide communications with the processing system 12.

If it is desired to detect a chemical or estimate the concentration of the chemical in a borehole fluid, then the downhole tool 10 may include openings to allow the borehole fluid to flow through the tool 10 and contact the sensor system 9. If it is desired to detect a chemical or estimate the concentration of the chemical in a formation fluid, then the downhole tool 10 may include a formation tester 13 as illustrated in FIG. 1. The formation tester 13 includes an extendable probe 14 and sealing pad 15 configured to extend from the tool 10 and seal to a wall of the borehole 2. Pressure is reduced within the probe 14, such as by a pump, drawing formation fluid into the tester 13 where it can be sensed by the sensor system 9.

Figure 2:
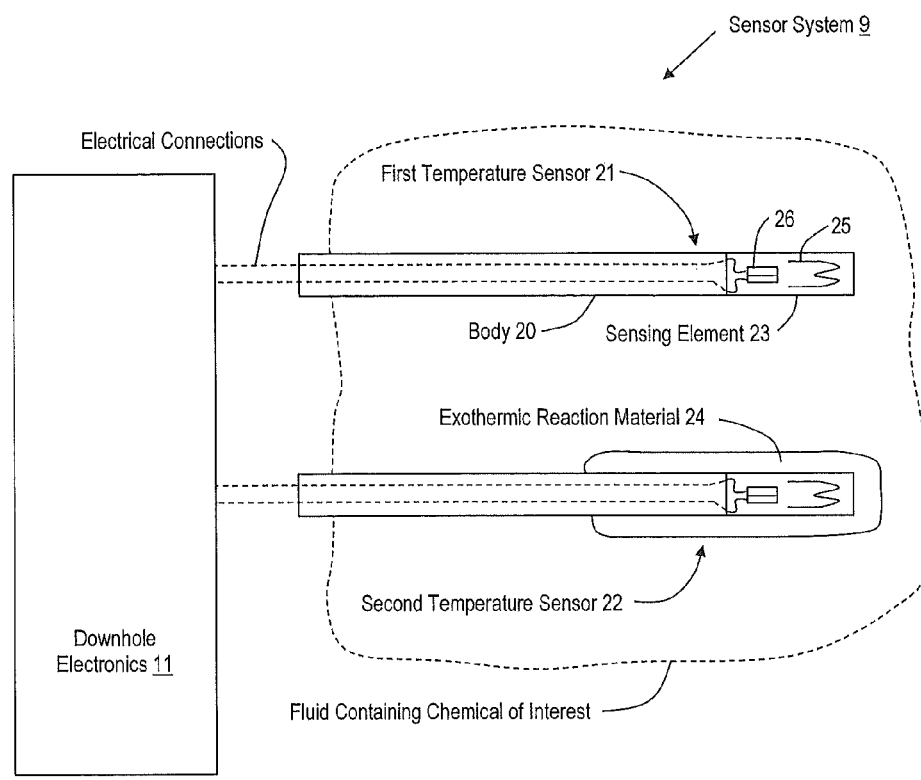
FIG. 2 depicts aspects of first and a second temperature sensors configured to detect a chemical in a fluid or estimate a concentration of the chemical in the fluid.

Reference may now be had to FIG. 2 depicting aspects of the sensor system 9 in a cross-sectional view. The sensor system 9 includes a first temperature sensor 21 and a second temperature sensor 22. Each of the temperature sensors 21 and 22 are configured to be immersed in the fluid and include a body 20 and a sensing element 23. In general, the sensing element 23 has a predictable change in a characteristic (e.g., an electrical characteristic) that corresponds to a change in temperature. In one or more embodiments, the sensing element 23 of each the temperature sensors 21 and 22 may be a resistance-temperature-detector (RTD) 25 or a thermocouple 26. In the embodiment of FIG. 2, the first temperature sensor 21 is uncoated and configured to sense the temperature of the fluid containing the chemical of interest. The second temperature sensor 22 is coated or covered with an exothermic reaction material 24 that undergoes an exothermic reaction when the material 24 comes into contact with the chemical of interest. Hence, when the first and second temperature sensors 21 and 22 are exposed to the fluid containing the chemical of interest, the first temperature sensor 21 will provide a measurement of the temperature of the fluid or a reference temperature and the second temperature sensor 22 will provide a measurement of a temperature that is higher than the reference temperature due to the exothermic reaction. If the chemical of interest is not present in the fluid, then the first and second temperature sensors 21 and 22 will read the same temperature. It can be appreciated that in one or more embodiments, the downhole electronics 11 may include a Wheatstone bridge to measure the voltage difference and thus the temperature difference between the first and second temperature sensors 21 and 22.

It can be appreciated that in one or more embodiments, the exothermic reaction material 24 may be in the form of a porous layer of nanoparticles. An advantage of the porous layer of nanoparticles is that it affords an increased contact area with the chemical of interest resulting in an increase in energy released from the exothermic reaction and increasing a temperature difference that may be measured to improve the accuracy of the measurement.

Figure 3:
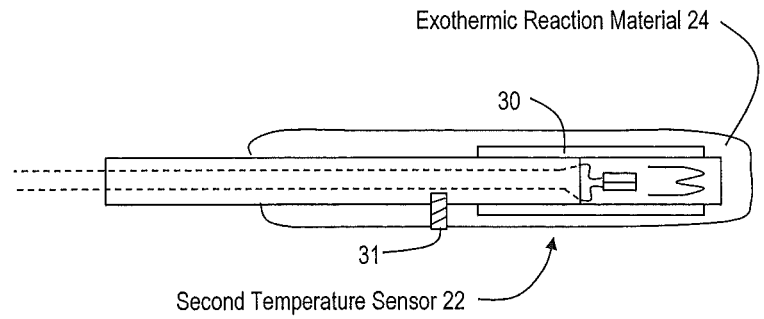
FIG. 3 depicts aspects of an exothermic reaction material covering a sensing element of the second temperature sensor.

In one or more embodiments, an adhesive 30, illustrated in FIG. 3, is used to adhere the exothermic reaction material 24 to the body or sensing element of the second temperature sensor 22. In one or more embodiments, a mechanical fastener 31, illustrated in FIG. 3, such as a threaded fastener is used to secure the exothermic reaction material 24 to the body or sensing element of the second temperature sensor 22.

In one or more embodiments, a difference in temperature measurements using sensors 21 and 22 that is above a noise level provides an indication that the chemical of interest has been detected. It can be appreciated that as the concentration of the chemical interest in the fluid increases, the exothermic reaction rate also increases and so generates energy at an increased rate. Hence, in one or more embodiments, the rate of change of the temperature read by the second sensor 22 referenced to the temperature read by the first sensor 21 provides an indication of the concentration of the chemical of interest. Sensors for the fluid's thermal conductivity, heat capacity, or convective flow past the sensor or for other properties can be used to adjust the inferred concentration. Alternatively, when a fluid sample is contained in a sample chamber (such as in the formation tester 13) so that there is little to no fluid flow by the sensors and consequently little or no heat transfer, then a temperature difference between the temperatures read by the first and second temperature sensors 21 and 22 at a certain point in time may provide an indication of the concentration of the chemical of interest in the fluid.

Figure 4:
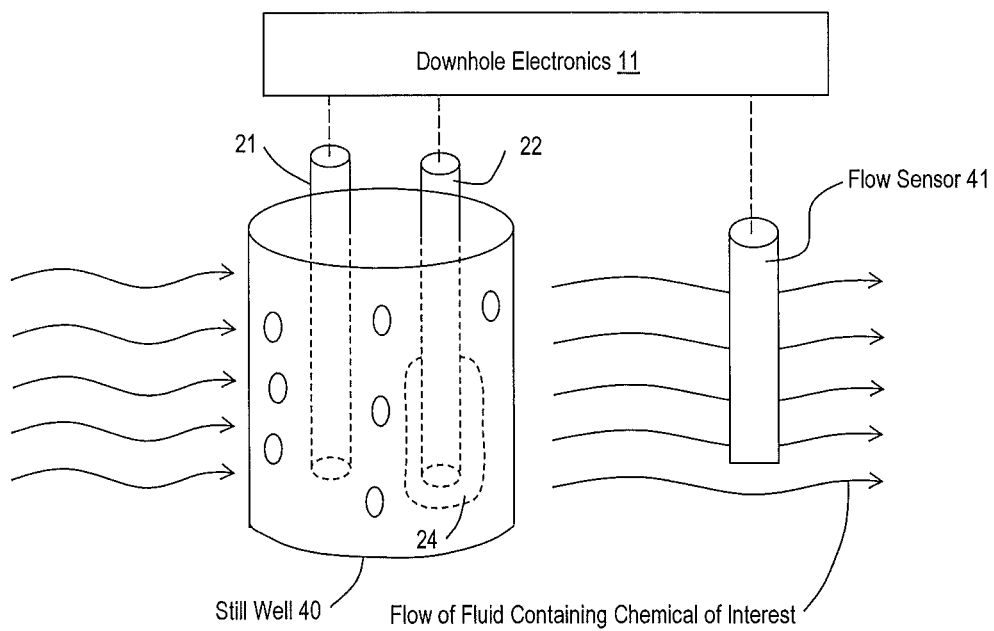
FIG. 4 depicts aspects of a still well and flow sensor used with the temperature sensors.

It can be appreciated that the flow of fluid by the second sensor 22 may increase the transfer of heat generated by the exothermic reaction and result in a lower temperature reading than if there was little or no flow. Hence, in one or more embodiments, at least the second temperature sensor 22 may be disposed in a still well 40 that is configured to slow the flow of fluid passing by the sensor 22 as illustrated in FIG. 4. It can be appreciated that beside the exothermic reaction rate, the flow rate of fluid by the second temperature sensor 22 may also affect the temperature read by the sensor 22. Consequently, a flow sensor 41 configured to sense a flow rate of fluid flowing by the sensor 22 may be included in the downhole tool 10 as illustrated in FIG. 4. Output from the flow sensor 22 may be input into the downhole electronics 11 in order to compensate for the flow and heat transfer rate in determining the concentration of the chemical of interest.

It can be appreciated that several factors may influence the determination of the chemical concentration. These factors include the flow rate of the fluid by the second temperature sensor 22, the heat capacity of the fluid, the chemical of interest, the exothermic reaction material 24, and the temperature of the fluid noting that the fluid temperature may influence the exothermic reaction rate. In order to accurately detect the chemical of interest or its concentration, the downhole tool 10 of a certain configuration may be calibrated in a test laboratory using expected values of the above factors for a selected concentration of a chemical of interest in an expected fluid and using a selected exothermic reaction material. The factor values may be varied over an expected range of values and the corresponding temperature sensor readings recorded to generate a lookup table. Hence, when the downhole tool 10 is deployed downhole, the sensed temperatures from the temperature sensors 21 and 22 along with the known factor values may be input into the lookup table to determine the concentration of the chemical of interest. Alternatively, a heat transfer analysis of the downhole tool 10 having a certain configuration, certain dimensions, and a selected exothermic reaction material may be performed for an expected chemical of interest in an expected fluid to calibrate the tool 10.

In one or more embodiments, the chemical of interest is hydrogen sulfide ($H_2S$) and the fluid is crude oil. Examples of exothermic reaction materials that react with $H_2S$ are metal oxides such as oxides of iron, zinc, calcium, or magnesium, for which the reaction with $H_2S$ is very exothermic. In general, commercial $H_2S$ scavenger materials react exothermically with $H_2S$. The reaction of $H_2S$ with ZnO is one of the most exothermic releasing 84 KJoules/mol, which is 20 Kcal/mol. Crude oil has a density of about 0.85 g/cc and $H_2S$ has a molecular weight of 34, so 1 ppm (part per million) of $H_2S$ by weight in crude oil is approximately 1 mg of $H_2S$ per $1/0.85$ liters of crude oil, which is $1/34000$ of a mole of $H_2S$ per 1.18 liters or 25 micromoles of $H_2S$ per liter of crude oil. If all the $H_2S$ reacted with ZnO, the released energy from the exothermic reaction would be [25 micromoles/liter]*[20 Kcal/mol]= 0.50 calories per liter of crude oil for every ppm of $H_2S$. In that a calorie is the heat needed to raise the temperature of 1 cc of water by 1 degree C. and that a quality platinum RTD sensor can resolve a temperature change of 0.001 degree C., the sensor system 9 is sensitive enough to measure the heat of reaction of several ppm of $H_2S$ in crude oil with a layer of ZnO that is covering the second temperature sensor 22.

Figure 5:
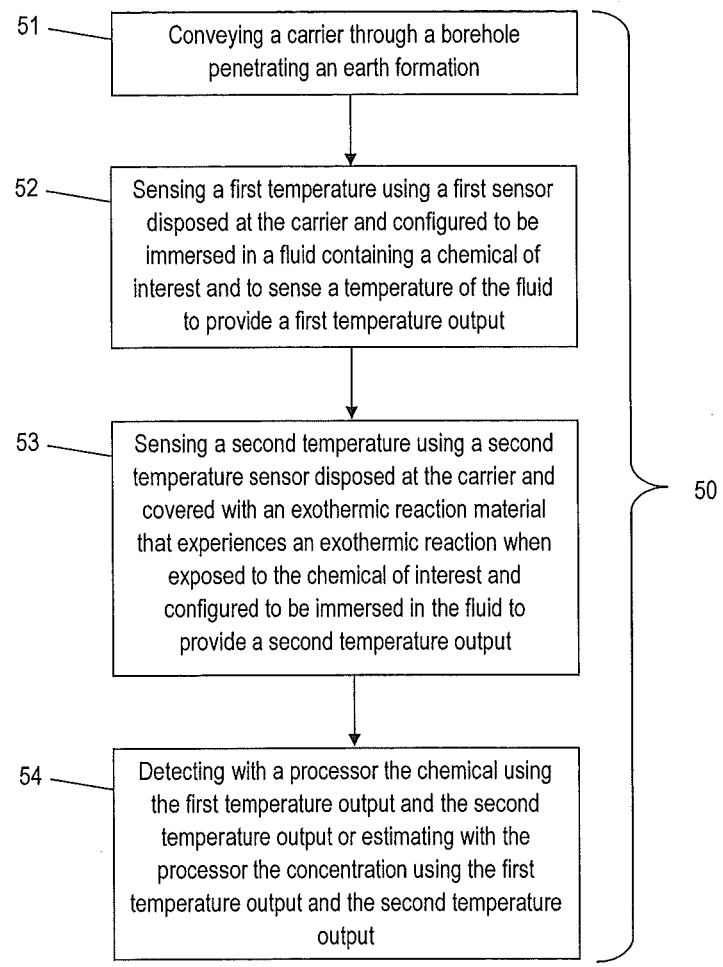
FIG. 5 is a flow chart of a method for detecting a chemical of interest in a fluid or estimating a concentration of the chemical in the fluid downhole.

FIG. 5 is a flow chart for a method 50 for detecting a chemical of interest in a fluid or estimating a concentration of the chemical of interest in the fluid. Block 51 calls for conveying a carrier through a borehole penetrating an earth formation. Block 52 calls for sensing a first temperature using a first sensor disposed at the carrier and configured to be immersed in the fluid and to sense a temperature of the fluid to provide a first temperature output. Block 53 calls for sensing a second temperature using a second temperature sensor disposed at the carrier and covered with an exothermic reaction material that experiences an exothermic reaction when exposed to the chemical of interest and configured to be immersed in the fluid to provide a second temperature output. Block 54 calls for detecting with a processor the chemical by using the first temperature output and the second temperature output or by estimating with the processor the concentration using the first temperature output and the second temperature output.

The above disclosed techniques provide several advantages. One advantage is that a membrane inlet transparent to the chemical of interest is not required, thus avoiding any inherent maintenance issues associated with its use. Further, the simplicity of the sensor system 9 makes it economical and provides for rugged construction that can endure the harsh environment experienced downhole.

In support of the teachings herein, various analysis components may be used, including a digital and/or an analog system. For example, the downhole electronics 11, the computer processing system 12, or the sensor system 9 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second" and the like do not denote a particular order, but are used to distinguish different elements.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for detecting a chemical of interest in a fluid or estimating a concentration of the chemical in the fluid, the apparatus comprising:
  a carrier configured to be conveyed through a borehole penetrating an earth formation;
  a first temperature sensor disposed at the carrier and configured to sense a temperature of the fluid and provide a first temperature output;
  a second temperature sensor disposed at the carrier and covered with an exothermic reaction material that experiences an exothermic reaction when exposed to the chemical of interest and configured to sense a temperature and provide a second temperature output; and
  a processor coupled to the first temperature sensor and the second temperature sensor and configured to detect the chemical or estimate the concentration using the first temperature output and the second temperature output.

2. The apparatus according to claim 1, wherein the chemical of interest is hydrogen sulfide.

3. The apparatus according to claim 1, wherein the fluid is a drilling fluid.

4. The apparatus according to claim 1, wherein the fluid is a formation fluid.

5. The apparatus according to claim 1, wherein the apparatus further comprises a non-transitory medium having instructions to cause the processor to calculate a difference between the second temperature output and the first temperature output and to use the difference to detect the chemical or estimate the concentration.

6. The apparatus according to claim 1, wherein the apparatus further comprises a non-transitory medium having instructions to cause the processor to calculate a rate of change of the second temperature output and to use the rate of change to detect the chemical or estimate the concentration.

7. The apparatus according to claim 1, further comprising a still well wherein at least the second temperature sensor is disposed within the still well and the still well is configured to decrease a flow rate of the fluid past the at least second temperature sensor.

8. The apparatus according to claim 1, further comprising a formation tester configured to extract a sample of the fluid from the earth formation wherein the first temperature sensor and the second temperature sensor are configured to be immersed in the sample.

9. The apparatus according to claim 1, wherein the exothermic reaction material comprises a porous layer of nanoparticles.

10. The apparatus according to claim 1, wherein the exothermic reaction material comprises a metal oxide.

11. The apparatus according to claim 9, wherein the metal oxide comprises at least one selection from a group consisting of iron, zinc, calcium and magnesium.

12. The apparatus according to claim 1, further comprising an adhesive configured to attach the exothermic reaction material to a body of the second temperature sensor.

13. The apparatus according to claim 1, further comprising a mechanical fastener configured to attach the exothermic reaction material to a body of the second temperature sensor.

14. The apparatus according to claim 1, wherein the first temperature sensor is a resistance temperature device or a thermocouple and the second temperature device is a resistance temperature device or a thermocouple.

15. The apparatus according to claim 1, further comprising a flow sensor configured to sense a flow rate of the fluid flowing past at least the second temperature sensor and using the sensed flow rate to estimate the concentration.

16. The apparatus according to claim 1, wherein the carrier comprises a wireline, a slickline, a drill string or coiled tubing.

17. A method for detecting a chemical of interest in a fluid or estimating a concentration of the chemical of interest in the fluid, the method comprising:

conveying a carrier through a borehole penetrating an earth formation;

sensing a first temperature using a first sensor disposed at the carrier and configured to be immersed in the fluid and to sense a temperature of the fluid to provide a first temperature output;

sensing a second temperature using a second temperature sensor disposed at the carrier and coated with an exothermic reaction material that experiences an exothermic reaction when exposed to the chemical of interest and configured to be immersed in the fluid to provide a second temperature output; and detecting with a processor the chemical using the first temperature output and the second temperature output or estimating with the processor the concentration using the first temperature output and the second temperature output.

18. The method according to claim 17, further comprising calculating a temperature difference between the second temperature sensor and the first temperature sensor and using the temperature difference to detect the chemical or estimate the concentration.

19. The method according to claim 17, further comprising calculating a rate of change of the second temperature and using the rate of change to detect the chemical or estimate the concentration.

20. The method according to claim 17, further comprising looking up in a lookup table the concentration based on the first temperature output and the second temperature output using the processor.

21. The method according to claim 20, measuring a flow rate of the fluid flowing past at least the second sensor using a flow sensor and wherein the concentration in the lookup table is further based on the flow rate.

* * * * *